United States Patent [19]

Schwender et al.

[11] 4,117,131

[45] Sep. 26, 1978

[54] METHOD OF INHIBITING GASTRIC ACID SECRETIONS WITH 2-(4-PYRIMIDINYL)THIOACETAMIDES

[75] Inventors: Charles F. Schwender, Dexter, Mich.; Russell E. Pike, Stanhope, N.J.

[73] Assignee: Warner-Lambert Company, Morris Plains, N.J.

[21] Appl. No.: 832,312

[22] Filed: Sep. 12, 1977

Related U.S. Application Data

[63] Continuation-in-part of Ser. No. 748,348, Dec. 7, 1976, abandoned.

[51] Int. Cl.$^2$ ............... A61K 31/505; C07D 239/00
[52] U.S. Cl. ............... 424/251; 544/301; 544/312; 544/319; 544/321; 544/302; 544/314; 544/320
[58] Field of Search ............... 424/251

[56] References Cited

U.S. PATENT DOCUMENTS

| | | | |
|---|---|---|---|
| 3,898,335 | 8/1975 | Loev | 424/251 |
| 3,907,814 | 9/1975 | Hoever et al. | 424/251 |

Primary Examiner—Frederick E. Waddell
Attorney, Agent, or Firm—Albert H. Graddis; Frank S. Chow; George M. Yahwak

[57] ABSTRACT

2-(4-Pyrimidinyl)thioacetamides are disclosed that have been found useful in the treatment of gastric hyperacidity.

11 Claims, No Drawings

METHOD OF INHIBITING GASTRIC ACID SECRETIONS WITH 2-(4-PYRIMIDINYL)THIOACETAMIDES

This application is a continuation-in-part of U.S. Patent Application Ser. No. 748,348, filed Dec. 7, 1976, now abandoned.

The present invention relates to the following generic series of compounds:

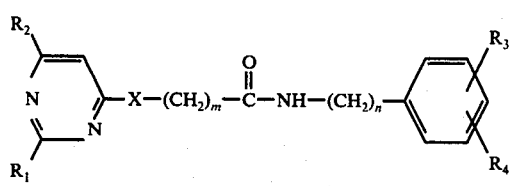

wherein $R_1$ and $R_2$ are selected from a group consisting of hydrogen, amino, alkylamino, hydroxyl, alkyl or alkoxy; wherein $R_3$ and $R_4$ are selected from a group consisting of hydrogen, alkyl, alkoxy, amino, alkylamino, halogen, hydroxy, methylenedioxy, phenoxy, phenyl, alkylthio, trifluoromethyl, alkylsulfonyl and alkylsulfinyl; wherein $m$ is 1-4, $n$ is 0-4, and $X$ is S or O. Also includes within the scope of the present invention are the pharmaceutically acceptable salts.

As used above, the terms alkyl and alkoxy refer to those chemical moieties containing 1 to 4 carbon atoms in either straight or branched configuration; the term halogen refers to fluoride, chloride, iodide, bromide, or iodide radicals.

The preferred species of this invention includes those analogs where $R_1 = NH_2$, $R_2 = CH_3$, $R_3R_4 = H$ and $m = 1$, $n = 2$
$R_1 = NH_2$, $R_2 = CH_3$, $R_3 = 4-OCH_3$, $R_4 = H$, $m = 1$, $n = 2$
$R_1 = NH_2$, $R_2 = CH_3$, $R_3R_4 = H$, $m = 1$, $n = 1$
$R_1 = NH_2$, $R_2 = CH_3$, $R_3 = 4-CH_3$, $R_4 = H$, $m = 1$, $n = 2$ The compounds of this invention may be prepared in two steps from readily available starting materials. The appropriately substituted 4-chloro-pyrimidine is reacted with 2-mercaptoacetate in an alcohol containing sodium alkoxide as base to give the intermediate 2-(4-pyrimidinyl)-thioacetate. Reaction of the acetate intermediate with the appropriate amine gives the desired compounds.

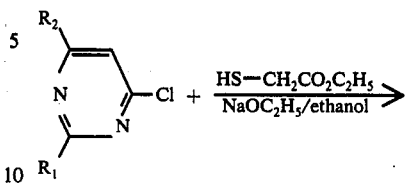

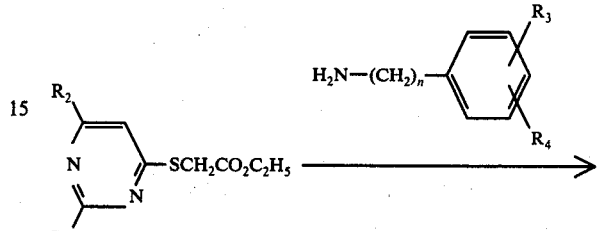

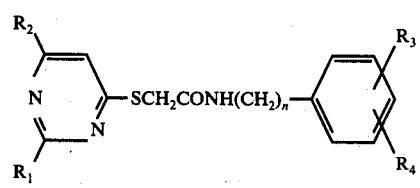

The analogs may also be prepared from the appropriately substituted 4-mercaptopyrimidine and the ω-haloalkanoate ester in an alcohol containing an alkoxide as base. The intermediate ester obtained is then reacted with the appropriate amine giving the compounds of this invention.

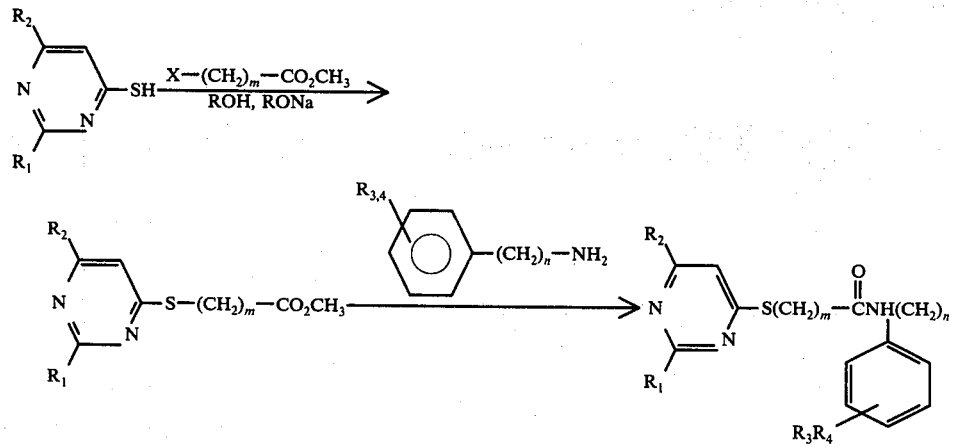

In another aspect of the invention, there is provided a pharmaceutical composition comprising a compound of formula I as has been defined or a pharmaceutically acceptable salt thereof together with a pharmaceutically acceptable carrier.

The pharmaceutically acceptable salts of the free compounds of general formula I may be prepared by conventional reactions with equivalent amounts of inorganic or organic acid solutions. As exemplary of pharmaceutically acceptable salts there are the salts of hydrochloric, hydrobromic, sulfuric, benzenesulphonic, acetic, oxalic, malic, and citric acids.

The compounds of general formula I, as well as their pharmaceutically acceptable inorganic and organic acid salts, may be administered enterally or parenterally in admixture with a liquid or solid pharmaceutical diluent or carrier. As injection medium it is preferred to use water which contains the conventional pharmaceutical advantages for injection solutions such as stabilizing agents, solubilizing agents and buffers, for example, ethanol, complex-forming agents such as ethylene diamine tetraacetic acid, tartrate, and citrate buffers and highly molecular weight polymers such as polyethylene oxide for viscosity regulation. Examples of carrier materials include starch, lactose, mannitol, methylcellulose, talc, highly dispersed silicic acids, high molecular weight fatty acids such as stearic acid, and high molecular weight polymers such as polyethylene glycols. Oral forms of administration may, of course, contain flavoring, sweetening, preserving, suspending, thickening, or emulsifying agents.

A particular aspect of the formula composition comprises a compound of formula I in an effective unit dose form. By "effective unit dose" is meant a predetermined amount sufficient to be effective to bring about the desired decrease in gastric acid secretion in vivo.

In yet a further aspect of the invention, there is provided a method of inhibiting gastric acid secretion in mammals, including man, which comprises the administration of an effective secretion inhibiting amount of a compound of general formula I or a pharmaceutically acceptable salt thereof.

It is believed that one of ordinary skill in the art, can, using the preceding description, utilize the present invention to its fullest extent. The following specific embodiments, are, therefore, to be simply construed as merely illustrative and not to limit the remainder of the specification and claims in any way whatsoever.

EXAMPLE 1

Ethyl 2-[(2-amino-6-methylpyrimidin-4-yl)thio]acetate

Sodium (4.6 g, 0.2 mol) was dissolved in 1 l. abs. EtOH. Ethyl mercaptoacetate (24 g, 0.2 mol) was added and the resultant mixture was stirred 1 hr. at room temperature. The 2-amino-4-chloro-6-methylpyrimidine (0.2 mol) was added and the mixture was heated at reflux for 18 hrs. The reaction mixture was evaporated to a syrupy residue which was portitioned between $CHCl_3$ (1.5 l.) and $H_2O$ (100 ml). The $CHCl_3$ phase was dried ($MgSO_4$) and evaporated to give the crude product as an oil, 40.6 g (91%). The straw colored oil crystallized upon standing, m.p. 65°–69°. The analytical sample was obtained by a recrystallization from cyclohexane, 27 g (60%), m.p. 71°–73°.

EXAMPLE 2

2-[(2-Amino-6-methyl-4-pyrimidinyl)thio]-N-(2-phenylethyl)acetamide

A mixture of 7.50 g (33.0 mmol) of ethyl 2-[(2-amino-6-methylpyrimidin-4-yl)thio]acetate, 4.40 g (36.3 mmol) of 2-phenylethylamine and 25 ml of MeOH was heated at 120° for 18 hrs. in a steel bomb. The reaction mixture was evaporated to a residual solid which yielded crude solid product (7.65 g, 76.7%), m.p. 114°–121° upon trituration with $Et_2O$. The analytically pure sample was obtained after one recrystallization from 2-propanol, m.p. 130°–132° (3.79 g, 38%).

EXAMPLE 3

Butyl 5-[(2-amino-6-methyl-4-pyrimidinyl)thio]valerate

To a solution of sodium (1.79 g, 77.9 mmol) dissolved in 500 ml of 1-buOH, was added 10.0 g (70.8 mmol) of 2-amino-4-methyl-6-mercaptopyrimidine and the resultant mixture was stirred at room temperature for ½ hour. After the addition of ethyl 5-bromovalerate (29.7 g, 142 mmol), the mixture was heated at reflux for 20 hrs. The mixture was then evaporated to a residual oil which was suspended between 1N HCl (500 ml) and ether (500 ml). The acidic phase was basified with $NH_4OH$ and extracted with $CHCl_3$ (1 l.). The $CHCl_3$ phase was dried ($MgSO_4$) and evaporated to give 16.8 g (79.6%) of a straw colored oil which solidified upon standing, m.p. 45°–47°. One recrystallization from hexane gave the analytical ester; yield, 11.1 g (52.6%), m.p. 50°–52°.

The various physical properties of the preferred compounds of this invention are tabulated in the following Table I:

TABLE I

| $R_1$ | $R_2$ | n | $R_3$ | $R_4$ | mp° C | Solvent Recrystal |
|---|---|---|---|---|---|---|
| $NH_2$ | $CH_3$ | 2 | H | H | 130 – 32 | 2-PrOH |
| $NH_2$ | $CH_3$ | 3 | H | H | 149 – 51 | 2-PrOH |
| $NH_2$ | $CH_3$ | 2 | 4-Cl | H | 168 – 70 | 2-PrOH |
| $NH_2$ | $CH_3$ | 2 | 4-$NH_2$ | H | 196 – 97 | 2-PrOH |
| $NH_2$ | $CH_3$ | 2 | 4-$CH_3$ | H | 178 – 79 | 2-PrOH |
| $NH_2$ | $CH_3$ | 2 | 3-$OCH_3$ | 4-$OCH_3$ | 141 – 42 | $CH_3CN$ |
| $NH_2$ | $CH_3$ | 2 | 4-$OCH_3$ | H | 147 – 49 | $CH_3CN$ |
| $NH_2$ | $CH_3$ | 2 | 3-Cl | H | 111 – 12 | $CH_3CN$ |
| $NH_2$ | $CH_3$ | 1 | H | H | 164 – 65 | 2-PrOH |
| $NH_2$ | $CH_3$ | 1 | 4-Cl | H | 192 – 94 | $CH_3CN$ |
| $NH_2$ | $CH_3$ | 1 | 4-$OCH_3$ | H | 152 – 53 | $CH_3CN$ |

| Structure | mp° C | Solvent Recrystal |
|---|---|---|
| $H_2N$–pyrimidine–$SCH_2CO_2C_2H_5$ | 135 – 37 | $C_6H_5CH_3$ |
| $CH_3$/$H_2N$-pyrimidine–$S(CH_2)_4CO_2C_4H_9$ | 50 – 52 | $C_6H_{14}$ |
| $H_3C$/$H_2N$-pyrimidine–$SCH_2CO_2C_2H_5$ | 71 – 73 | $C_6H_{12}$ |

The compounds of this invention having the generic structure above, have been found to reduce gastric acid secretion response due to 4-methylhistamine, an $H_2$-agonist when tested in accordance with the procedures of Shay (Gastroenterology 5:43, 1945) and Grossman (Gastroenterology 38:343, 1960). The compounds are active when administered orally and parenterally in mammals such as rats and dogs throughout a dosage range of 0.05 – 20 mg/kg. The compounds of this invention have been found not to act by an anticholinergic mechanism and therefore side effects observed in currently used therapy such as dryness of mouth or blurred vision does not occur. The compounds of this invention are useful in the management and treatment of gastric hyperacidity.

As stated earlier, the compounds of this invention are suitably and generally administered in oral dosage form, such as by tablet or capsule, by combining the same in an effective amount with any oral pharmaceutically acceptable inert diluent, such as lactose, starch, dicalcium phosphate, calcium sulfate, kaolin, mannitol and powdered sugar. In addition, when required, suitable binders, lubricants, disintegrating agents, and coloring agents can also be added. Typical binders include starch, gelatin, sugars such as sucrose, molasses, and lactose, natural and synthetic gums such as acacia sodium alginate, extract of Irish moss, carboxymethyl cellulose, methylcellulose, and polyvinylpyrrolidone, polyethylene glycol, ethylcellulose, and waxes. Typical lubricants for use in these dosage forms can include, without limitation, boric acid, sodium benzoate, sodium acetate, sodium chloride, leucine, and polyethylene glycol. Suitable disintegrators can include, without limitation, starch, methyl cellulose, agar, bentonite, cellulose and wood products, alginic acid, guar gum, citris pulp, carboxymethyl cellulose, and sodium lauryl sulfate. If desired, conventionally pharmaceutically acceptable dyes such as any of the standard FD & C dyes may be incorporated into the dosage unit form.

From the foregoing description, one skilled in the art can easily ascertain the essential characteristics of this invention and without departing from the spirit and scope thereof can make various changes and/or modifications to the invention for adapting it to various usages and conditions. Accordingly, such changes and modifications are probably intended to be within the full range of equivalents of the following claims.

We claim:

1. A method of inhibiting gastric acid secretions in a mammal which comprises the administration to a mammal of a pharmaceutical composition comprising a compound of the formula:

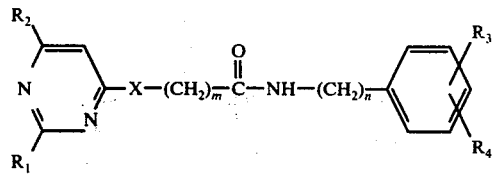

wherein $R_1$ and $R_2$ are selected from the group consisting of hydrogen, amino, alkylamino, hydroxyl, alkyl, and alkoxy; wherein $R_3$ and $R_4$ are selected from the group consisting of: hydrogen, alkyl, alkoxy, amino, alkylamino, halogen, hydroxy, methylenedioxy, phenoxy, phenyl, alkylthio, trifluoromethyl, alkylsulfonyl, and alkylsulfinyl;

wherein $m$ is 1 to 4 methylenes; wherein $n$ is 0 to 4 methylenes; wherein X is O or S; wherein alkyl and alkoxy are defined as having 1 to 4 carbon atoms; and the pharmaceutically acceptable salts thereof in an amount sufficient to decrease gastric acid secretions in said mammal.

2. The method according to claim 1 wherein the compound is 2-[(2-amino-6-methyl-4-pyrimidinyl)thio]-N-phenethyl-acetamide.

3. The method according to claim 1 wherein the compound is 2-[2-amino-6-methyl-4-pyrimidinyl)thio]-N-(3-phenylpropyl)acetamide.

4. The method according to claim 1 wherein the compound is 2-[(2-amino-6-methyl-4-pyrimidinyl)thio]-N-[2-(4-methylphenyl)ethyl]acetamide.

5. The method according to claim 1 wherein the compound is 2-[(2-amino-6-methyl-2-pyrimidinyl)thio]-N-[2-(4-methoxyphenyl)ethyl]acetamide.

6. The method according to claim 1 wherein the compound is 2-[(2-amino-6-methyl-4-pyrimidinyl)thio]-N-[2-(3,4-dimethoxyphenyl)ethyl]acetamide.

7. The method according to claim 1 wherein the compound is 2-[(2-amino-6-methyl-4-pyrimidinyl)thio]-N-[(4-chlorophenyl)methyl]acetamide.

8. The method according to claim 1 wherein the compound is 2-[(2-amino-6-methyl-4-pyrimidinyl)thio]-N-[(4-methoxyphenyl)methyl]acetamide.

9. The method according to claim 1 wherein the compound is 2-[(2-amino-6-methyl-4-pyrimidinyl)thio]-N-(phenylmethyl)acetamide.

10. The method according to claim 1 wherein the compound is 2-[(2-amino-6-methyl-4-pyrimidinyl)thio]-N-[2-(4-aminophenyl)ethyl]acetamide.

11. The method according to claim 1 wherein the compound is 2-[(2-amino-6-methyl-4-pyrimidinyl)thio]-N-[2-(4-chlorophenyl)ethyl]acetamide.

* * * * *